United States Patent [19]
Endres et al.

[11] Patent Number: 5,527,302
[45] Date of Patent: Jun. 18, 1996

[54] CONFORMABLE ABSORBENT ARTICLE

[75] Inventors: Dan D. Endres, Appleton; Timothy J. Blenke; Robert E. Vogt, both of Neenah; Georgia L. Zehner, Larsen; Steven H. Levine, Neenah; David P. Kielpikowski, Appleton; John P. Vukos; Mary A. Bruemmer, both of Neenah, all of Wis.

[73] Assignee: Kimberly-Clark Corporation, Neenah, Wis.

[21] Appl. No.: 14,045

[22] Filed: Feb. 5, 1993

Related U.S. Application Data

[63] Continuation of Ser. No. 826,309, Jan. 24, 1992, abandoned, which is a continuation of Ser. No. 452,867, Dec. 19, 1989, abandoned.

[51] Int. Cl.⁶ .................................................... A61F 13/15
[52] U.S. Cl. ................................. 604/385.1; 604/385.2; 604/391; 604/382
[58] Field of Search ........................ 604/358, 385.1, 604/385.2, 378–384, 386, 391

[56] References Cited

U.S. PATENT DOCUMENTS

| | | | |
|---|---|---|---|
| 1,977,604 | 10/1934 | Alsop | 128/284 |
| 2,026,158 | 12/1935 | Bennett | 128/290 |
| 2,074,936 | 3/1937 | Paterson | 128/286 |
| 2,104,423 | 1/1938 | Hughes | 128/290 |
| 2,141,205 | 12/1938 | Eller et al. | 128/284 |
| 2,837,095 | 6/1958 | Stevenson | 128/284 |
| 3,236,238 | 2/1966 | Morse | 128/290 |
| 3,262,451 | 7/1966 | Morse | 128/290 |
| 3,322,122 | 5/1967 | Daniel | 128/284 |
| 3,522,808 | 8/1970 | Worcester | 128/286 |
| 3,532,093 | 10/1970 | Lovret | 128/286 |
| 3,561,446 | 2/1971 | Jones, Sr. | 128/287 |
| 3,572,342 | 3/1971 | Lindquist et al. | 128/287 |
| 3,575,174 | 4/1971 | Mogor | 128/290 |
| 3,626,943 | 12/1971 | Worcester | 128/286 |
| 3,665,920 | 5/1972 | Davis | 128/287 |
| 3,779,246 | 12/1973 | Mesek et al. | 128/287 |
| 3,805,790 | 4/1974 | Kaczmarzyk et al. | 128/290 R |

(List continued on next page.)

FOREIGN PATENT DOCUMENTS

| | | |
|---|---|---|
| 888776 | 8/1981 | Belgium . |
| 143188 | 10/1990 | China . |
| 0109126A1 | 5/1984 | European Pat. Off. . |
| 0226789A3 | 7/1987 | European Pat. Off. . |
| 0263720A1 | 4/1988 | European Pat. Off. . |
| 0269401A2 | 6/1988 | European Pat. Off. . |
| 0323634A2 | 7/1989 | European Pat. Off. . |
| 0359410A1 | 3/1990 | European Pat. Off. . |
| 0357298A2 | 3/1990 | European Pat. Off. . |
| 038202A2 | 8/1990 | European Pat. Off. . |
| 0396050A2 | 11/1990 | European Pat. Off. . |
| 0403832A1 | 12/1990 | European Pat. Off. . |
| 2561078 | 9/1985 | France . |
| 2573629 | 5/1986 | France . |
| 2606257A1 | 5/1988 | France . |
| 62-88704 | 6/1987 | Japan . |
| 63-102704 | 7/1988 | Japan . |
| 63-162807 | 10/1988 | Japan . |
| H1-94403 | 6/1989 | Japan . |
| 2209672 | 5/1989 | United Kingdom . |
| 2216393A | 10/1989 | United Kingdom . |
| 2233876A | 1/1991 | United Kingdom . |
| 84/04242 | 11/1984 | WIPO . |

Primary Examiner—Randall L. Green
Assistant Examiner—K. M. Reichle
Attorney, Agent, or Firm—Jeffrey B. Curtin

[57] ABSTRACT

A conformable absorbent article has a topsheet that is designed to substantially fully contact the body of the wearer to provide improved performance in managing and containing body wastes. Management and containment of body wastes are improved by several structural elements that can be utilized individually or collectively. Some of these elements are a waste-containment pocket formed between the topsheet and backsheet, an opening in the topsheet for receiving body wastes therethrough, a pair of containment flaps and a pair of side flaps, and an expandable backsheet to retain body wastes therein.

16 Claims, 7 Drawing Sheets

U.S. PATENT DOCUMENTS

| | | | |
|---|---|---|---|
| 3,860,003 | 1/1975 | Buell | 604/385.2 |
| 3,881,489 | 5/1975 | Hartwell | 128/287 |
| 3,890,973 | 6/1975 | Davis et al. | 128/286 |
| 3,989,867 | 11/1976 | Sisson | 428/132 |
| 4,031,897 | 6/1977 | Graetz | 128/286 |
| 4,119,450 | 10/1978 | Bianco | 156/199 |
| 4,205,679 | 6/1980 | Repke et al. | 128/287 |
| 4,230,113 | 10/1980 | Mehta | 128/287 |
| 4,285,342 | 8/1981 | Mesek | 128/287 |
| 4,352,355 | 10/1982 | Mesek et al. | 128/287 |
| 4,388,075 | 6/1983 | Mesek et al. | 604/385 |
| 4,397,645 | 8/1983 | Buell | 604/380 |
| 4,430,086 | 2/1984 | Repke | 604/385 |
| 4,475,912 | 10/1984 | Coates | 604/385 |
| 4,554,191 | 11/1985 | Korpman | 428/35 |
| 4,579,556 | 4/1986 | McFarland | 604/385.2 |
| 4,591,523 | 5/1986 | Thompson | 428/131 |
| 4,610,682 | 9/1986 | Kopp | 604/385 R |
| 4,626,305 | 12/1986 | Suzuki et al. | 156/164 |
| 4,636,207 | 1/1987 | Buell | 604/370 |
| 4,639,949 | 2/1987 | Ales et al. | 2/400 |
| 4,642,819 | 2/1987 | Ales et al. | 2/400 |
| 4,646,362 | 3/1987 | Heran et al. | 2/400 |
| 4,655,760 | 4/1987 | Morman et al. | 604/385 A |
| 4,661,102 | 4/1987 | Shikata et al. | 604/385 A |
| 4,662,877 | 5/1987 | Williams | 604/385 A |
| 4,675,015 | 6/1987 | Brown | 604/385 R |
| 4,681,581 | 7/1987 | Coates | 604/391 |
| 4,685,916 | 8/1987 | Enloe | 604/385 A |
| 4,687,477 | 8/1987 | Suzuki et al. | 604/385 A |
| 4,695,278 | 9/1987 | Lawson | 604/385.2 |
| 4,701,171 | 10/1987 | Boland et al. | 604/385 A |
| 4,701,177 | 10/1987 | Ellis et al. | 604/385 A |
| 4,704,114 | 11/1987 | Wilson et al. | 604/385 A |
| 4,704,116 | 11/1987 | Enloe | 604/385.2 |
| 4,710,187 | 12/1987 | Boland et al. | 604/385 A |
| 4,713,069 | 12/1987 | Wang et al. | 604/378 |
| 4,728,326 | 3/1988 | Gilles | 604/391 |
| 4,731,066 | 3/1988 | Korpman | 604/366 |
| 4,738,677 | 4/1988 | Foreman | 604/385 R |
| 4,743,246 | 5/1988 | Lawson | 604/385 A |
| 4,773,906 | 9/1988 | Krushel | 604/391 |
| 4,775,375 | 10/1988 | Aledo | 604/378 |
| 4,778,459 | 10/1988 | Fuisz | 604/378 |
| 4,795,452 | 1/1989 | Blaney et al. | 604/385.1 |
| 4,795,454 | 1/1989 | Dragoo | 604/385.2 |
| 4,822,435 | 4/1989 | Igaue et al. | 156/164 |
| 4,834,737 | 5/1989 | Khan | 604/385.2 |
| 4,834,740 | 5/1989 | Suzuki et al. | 604/385.2 |
| 4,846,823 | 7/1989 | Enloe | 604/385.2 |
| 4,857,067 | 8/1989 | Wood et al. | 604/389 |
| 4,861,652 | 8/1989 | Lippert et al. | 428/284 |
| 4,872,871 | 10/1989 | Proxmire et al. | 604/394 |
| 4,880,420 | 11/1989 | Pomparelli | 604/385.1 |
| 4,880,421 | 11/1989 | Widlund | 604/385.2 |
| 4,883,480 | 11/1989 | Huffman et al. | 604/385.1 |
| 4,883,482 | 11/1989 | Gandrez et al. | 604/385.2 |
| 4,887,602 | 12/1989 | O'Leary | 604/305.1 |
| 4,892,528 | 1/1990 | Suzuki et al. | 604/395.2 |
| 4,892,536 | 1/1990 | DesMarais et al. | 604/385.2 |
| 4,895,568 | 1/1990 | Enloe | 604/385.2 |
| 4,904,251 | 2/1990 | Igaue et al. | 604/385.2 |
| 4,909,803 | 3/1990 | Aziz et al. | 604/385.2 |
| 4,916,005 | 4/1990 | Lippert et al. | 428/192 |
| 4,917,696 | 4/1990 | De Jonckheere | 604/385.2 |
| 4,936,840 | 6/1990 | Proxmire | 604/385.2 |
| 4,938,753 | 7/1990 | Van Gompel et al. | 604/385.2 |
| 4,938,754 | 7/1990 | Mesek | 604/385.2 |
| 4,938,757 | 7/1990 | Van Gompel et al. | 604/396 |
| 4,940,464 | 7/1990 | Van Gompel et al. | 604/396 |
| 4,950,262 | 8/1990 | Takagi | 604/385.1 |
| 4,968,312 | 11/1990 | Khan | 604/388.1 |
| 4,973,326 | 11/1990 | Wood et al. | 604/391 |
| 4,978,570 | 12/1990 | Heyn et al. | 428/231 |
| 4,981,480 | 1/1991 | Gaudet et al. | 604/386 |
| 4,988,344 | 1/1991 | Reising et al. | 604/368 |
| 4,988,346 | 1/1991 | Pfefferkorn | 604/389 |
| 4,988,560 | 1/1991 | Meyer et al. | 428/297 |
| 4,990,147 | 2/1991 | Freeland | 604/385.2 |
| 4,994,054 | 2/1991 | Pigneul et al. | 604/391 |
| 5,019,073 | 5/1991 | Roessler et al. | 604/391 |
| 5,037,416 | 8/1991 | Allen | 604/385.2 |
| 5,098,423 | 3/1992 | Pieniak et al. | 604/385.1 |
| 5,176,672 | 1/1993 | Bruemmer et al. | 604/385.1 |
| B1 3,860,003 | 4/1989 | Buell | 604/385.2 |
| B1 4,636,207 | 11/1989 | Buell | 604/370 |

CONFORMABLE ABSORBENT ARTICLE

BACKGROUND OF THE INVENTION

This is a continuation of application Ser. No. 07/826,309 filed on Jan. 24, 1992 which is a continuation of Ser. No. 07/452,867 filed on Dec. 19, 1989, both now abandoned.

This invention pertains to absorbent articles, and more particularly to an improved disposable absorbent article that easily and closely conforms to the body, specifically in the perineum area, of the wearer to provide improved performance in managing and containing body wastes.

Currently, disposable absorbent articles find wide spread use in infant, child, and adult incontinence care, and have generally replaced reusable cloth absorbent articles. A typical disposable absorbent article is a three-layered composite structure comprising a topsheet material, a backsheet material, and an absorbent material disposed therebetween.

One problem with current absorbent articles is the amount of skin area within the article that is exposed to body waste material. For example, current baby diapers are generously cut wider in the crotch area to assist in urine and BM management. This results in excess material bunching together between the legs, which can be extremely uncomfortable to the wearer. This bunching of material is further exacerbated by the elastication of the diaper edges. Consequently, the topsheet is prevented from being in close contact with the perineum area, thereby resulting in loss of management and containment of the flow of waste material between the body orifices and topsheet surface which in turn results in the spreading of waste material along the topsheet surface and against the wearer's skin.

Another problem with current absorbent articles is that leg movements over a period of time against the excess material between the legs can cause the absorbent to break apart, thereby decreasing its absorbent effectiveness.

Yet another problem with excess material between the legs is that the churning movement of the legs on the bunched-up material in the crotch causes the article to be pulled down from the crotch area, thereby further increasing the bunching problem and exposing additional skin area to fecal matter.

Still another problem is that excess material between the legs allows shifting or moving of the article in the crotch area, thereby further increasing problems with skin exposure to waste.

These problems generally result in skin dermatitis, skin hydration, and/or messy clean-ups.

SUMMARY OF THE INVENTION

In one embodiment of the invention, there is provided a disposable absorbent article comprising a liquid permeable topsheet having a topsheet peripheral measurement, and a liquid impermeable backsheet having a backsheet peripheral measurement that is greater than the topsheet peripheral measurement. The topsheet periphery and the backsheet periphery are joined together to form a waste containment pocket therebetween. The liquid permeable topsheet has an opening therein and is adapted to substantially fully contact the body of the wearer.

In another embodiment of the invention, there is provided a disposable absorbent article comprising a liquid permeable topsheet, a liquid impermeable backsheet, and an absorbent between the topsheet and backsheet, a pair of containment flaps positioned near the lateral sides of the topsheet, and a pair of side flaps positioned near the lateral sides of the topsheet.

In yet another embodiment of the present invention, there is provided a disposable absorbent article comprising a topsheet having a topsheet peripheral measurement, a backsheet having a backsheet peripheral measurement, and an absorbent structure between the topsheet and the backsheet. The backsheet is expandable so that upon receiving body wastes, the backsheet expands for the containment thereof.

BRIEF DESCRIPTION OF THE DRAWINGS

The above-mentioned and other features and objects of this invention, and the manner of attaining them, will become more apparent and the invention itself will be better understood by reference to the following description of the embodiment of the invention taken in conjunction with the accompanying drawings, wherein.

DETAILED DESCRIPTION

Figure 1:
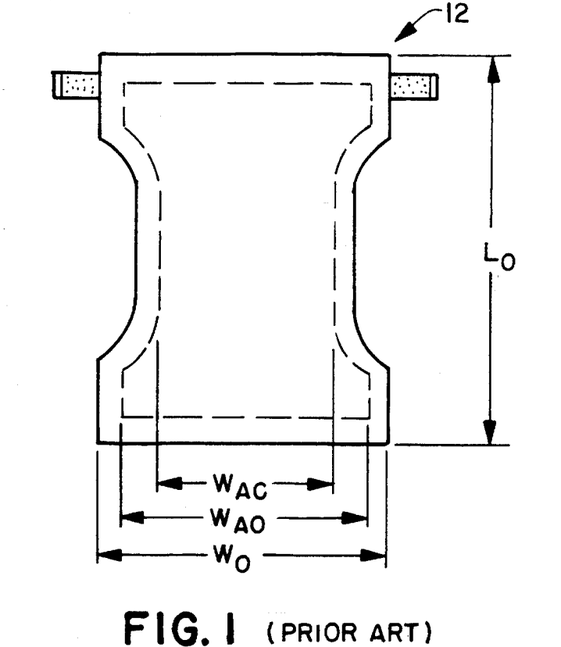
FIG. 1 is a top plan view of a prior art diaper.
Figure 2:
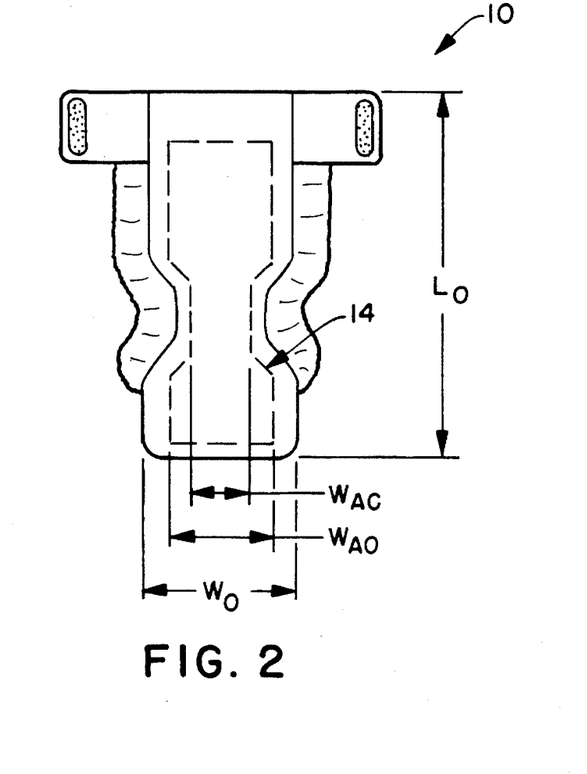
FIG. 2 is a top plan view of a diaper of the present invention.

The absorbent article of the present invention can be utilized as a baby diaper, adult incontinence garment, feminine care product, and the like. For purposes of the present discussion, the absorbent article will be described in terms of a baby diaper designed to fit a baby weighing between about 12 to about 24 pounds, but it is understood that the features and principles of the present invention apply to other baby sizes. As illustrated in FIGS. 1 and 2, disposable diaper 10 of the present invention is much smaller in size than a conventional diaper 12 of the prior art. Specifically, the overall length, $L_0$, of diaper 10 of the present invention is about 14 inches to about 15 inches; while the overall length, $L_0$, of conventional diaper 12 is about 17 inches to about 18 inches. The overall width, $W_o$, of diaper 10 is about 5 inches to about 8 inches; while the overall width, $W_o$, of conventional diaper 12 about 12 inches to about 13 inches. The overall width, $W_{AO}$, of absorbent structure 14 of diaper 10 is about 4 inches to about 7 inches; compared to the overall width, $W_{AO}$, of about 10 inches to about 11 inches of conventional diaper 12. The width of the absorbent at the crotch, $W_{AC}$, of diaper 10 is from about 2 inches to about 3 inches; while the absorbent width at the crotch, $W_{AC}$, of conventional diaper 12 is about 5 inches to about 6 inches.

Figure 3A:
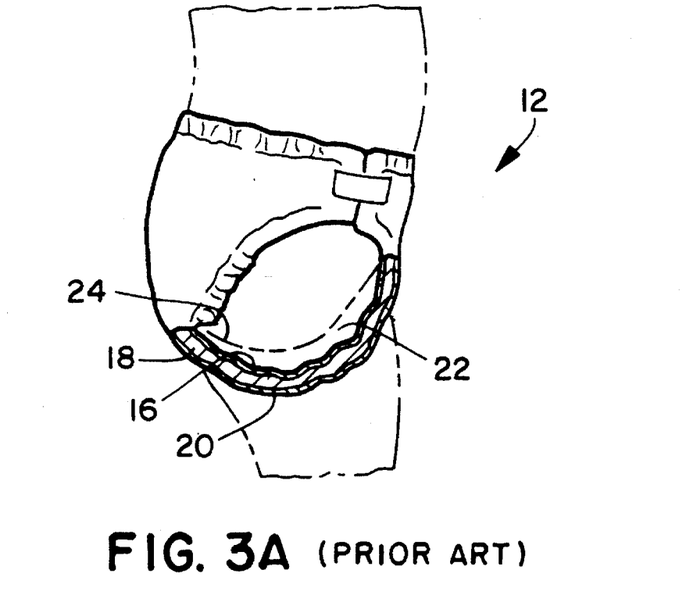
FIG. 3A is a side view of the prior art diaper in FIG. 1 as it would appear being worn.
Figure 3B:
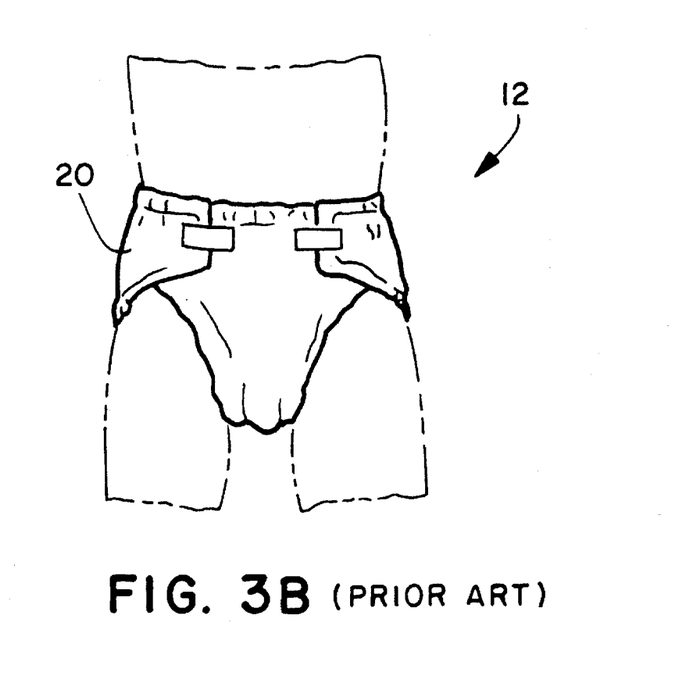
FIG. 3B is a front view of the prior art diaper in FIG. 1 as it would appear being worn.

Having compared the two diapers in size, a comparison of how they generally fit a baby is illustrated in FIGS. 3A–4B. In FIGS. 3A and 3B, conventional diaper 12 is being worn by a baby having a weight between about 12 to about 24 pounds. As illustrated, topsheet 16, absorbent 18, and backsheet 20 of conventional diaper 12 are bunched up and spaced away from crotch 24 forming a space 22 between crotch 24 and diaper 12. It is this forming of space 22 that causes loss of management and containment of waste material. The waste material spreads along topsheet 16 and contacts a large area of the baby's skin during movement of the baby. The bunching of topsheet 16, absorbent 18, and backsheet 20 at crotch 24 can cause breaking up of the absorbent material from leg movements, drooping of the diaper in the crotch, and shifting of the diaper on the baby.

Figure 4A:
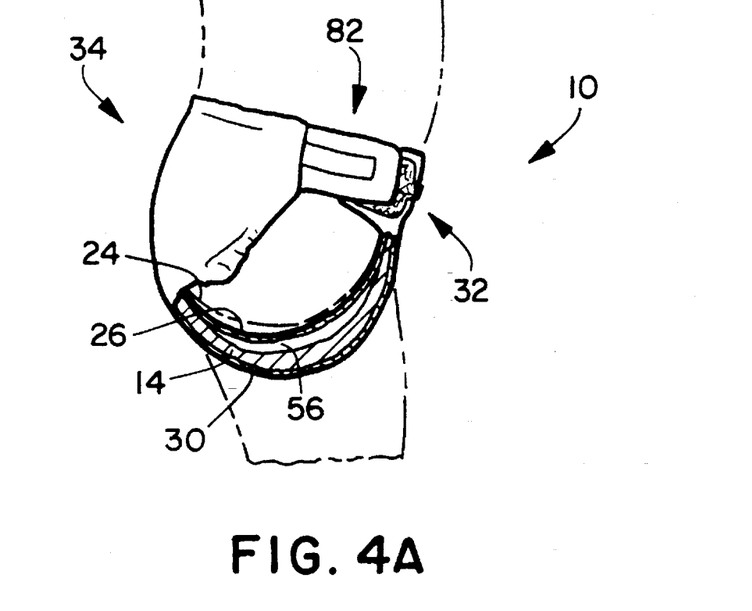
FIG. 4A is a side view of a diaper of the present invention in FIG. 8 as it would appear being worn.
Figure 4B:
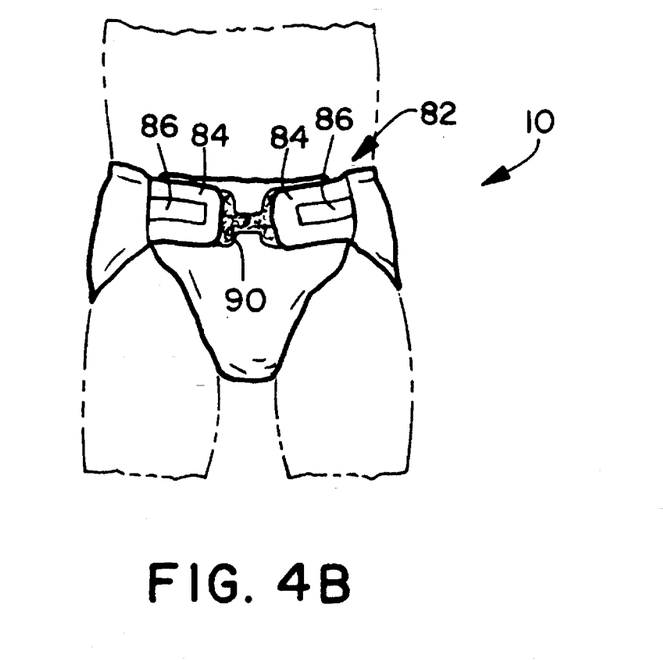
FIG. 4B is a front view of the embodiment of the present invention in FIG. 8 as it would appear being worn.

Referring to FIGS. 4A–B, topsheet 26, absorbent structure 14, and backsheet 30 of diaper 10 of the present invention are positioned in crotch 24 such that topsheet 26 substantially fully contacts the baby, particularly at crotch 24, thereby virtually eliminating or minimizing space 22. Topsheet contact with the body along a line centered or measured through crotch 24 from below the naval to the small of the back is important to positioning an opening or BM containment device in or associated with topsheet 26 relative to the anus to allow containment of feces under topsheet 26 or in the device. It is also important in urine control or management for immediate penetration through topsheet 26, thereby preventing urine from flowing over the topsheet surface. Two methods to obtain the preferred body contact with topsheet 26 are, first, cut and/or elastically narrow topsheet 26 to fit the crotch dimensions; and second, form the absorbent crotch width to have a width from about 2 inches to about 3 inches to allow the diaper to fit up between the baby's legs.

Figure 5:
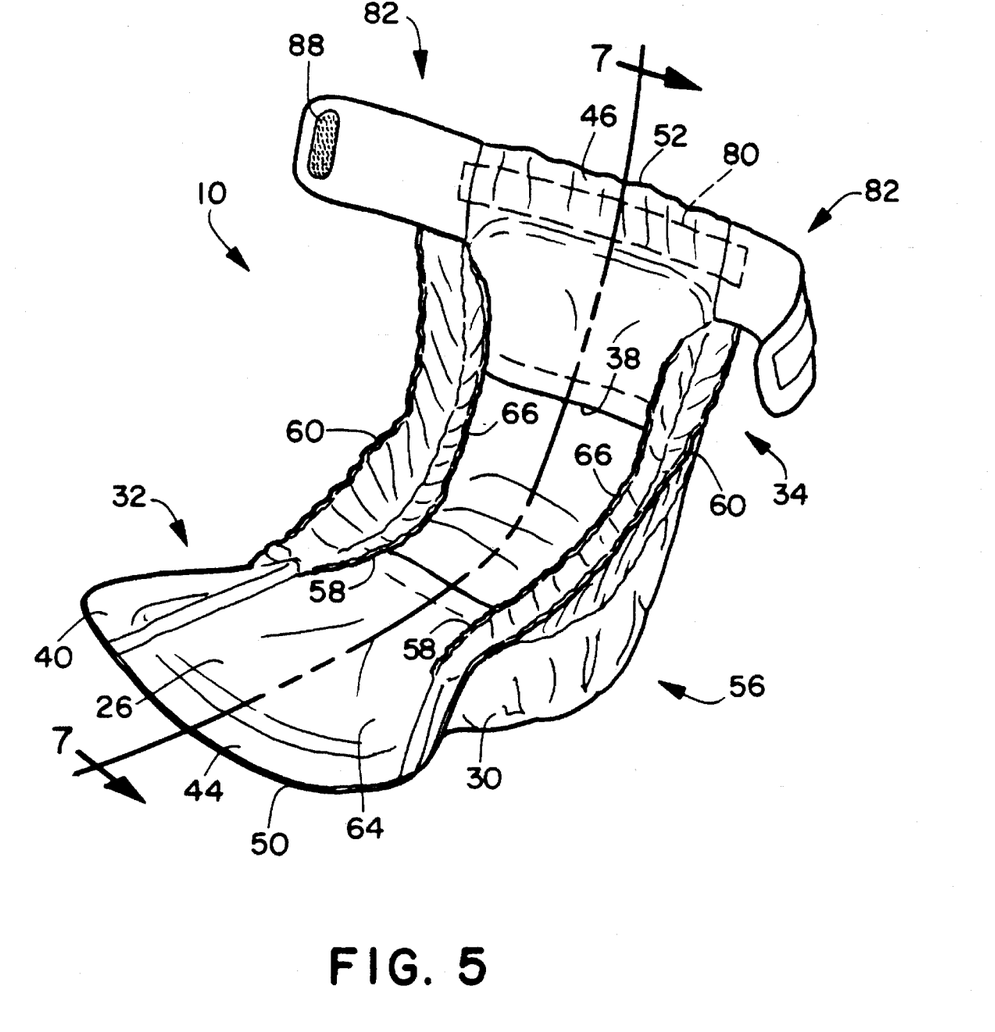
FIG. 5 is a perspective view of the embodiment of the present invention in FIG. 8 in its relaxed state.
Figure 6:
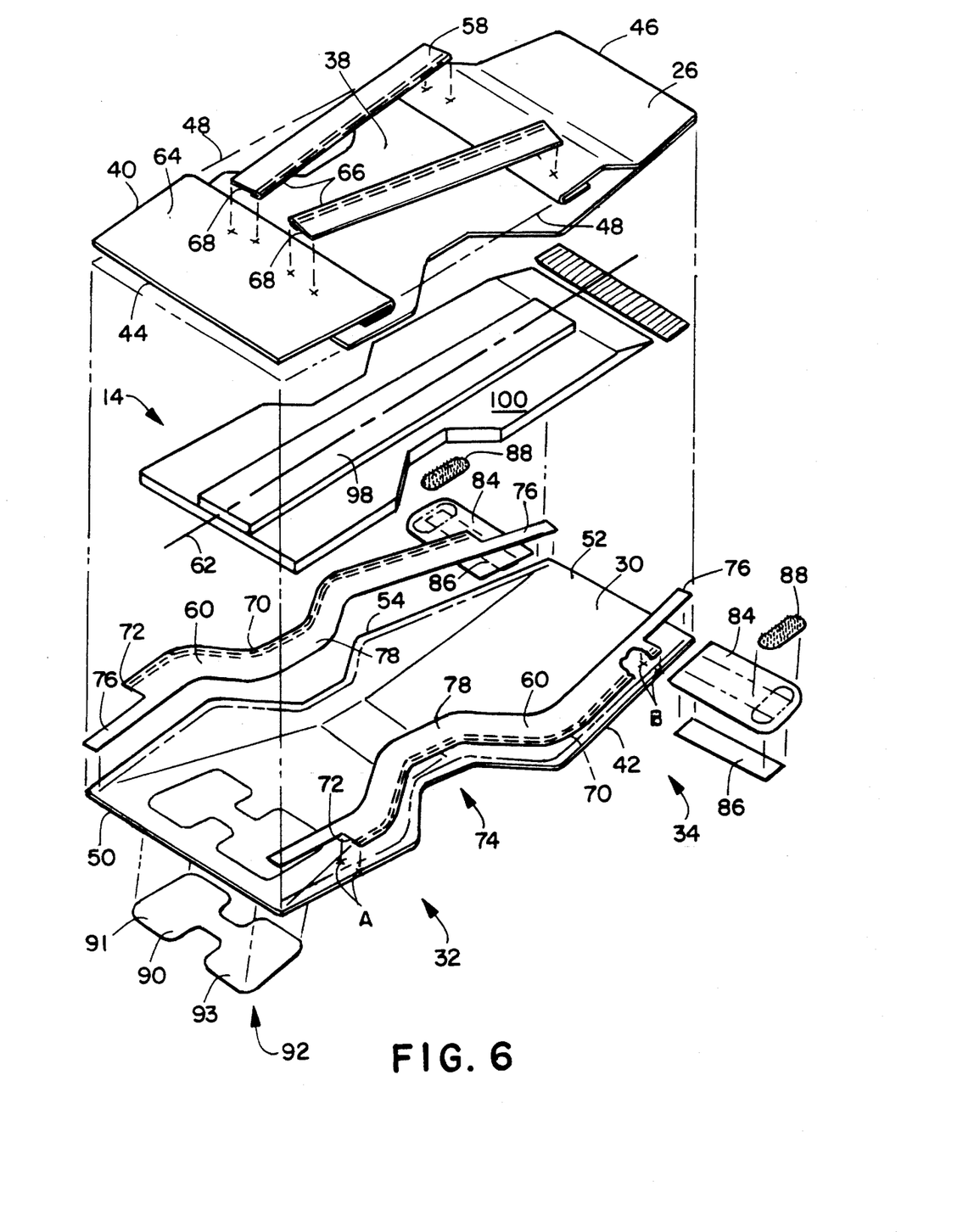
FIG. 6 is an exploded and partially broken-away view of the embodiment of the present invention in FIG. 8.

Referring to FIGS. 5 and 6, diaper 10 generally comprises liquid-permeable topsheet 26 having an opening 38 therein, liquid-impermeable backsheet 30, and absorbent structure 14 positioned therebetween.

Figure 7:
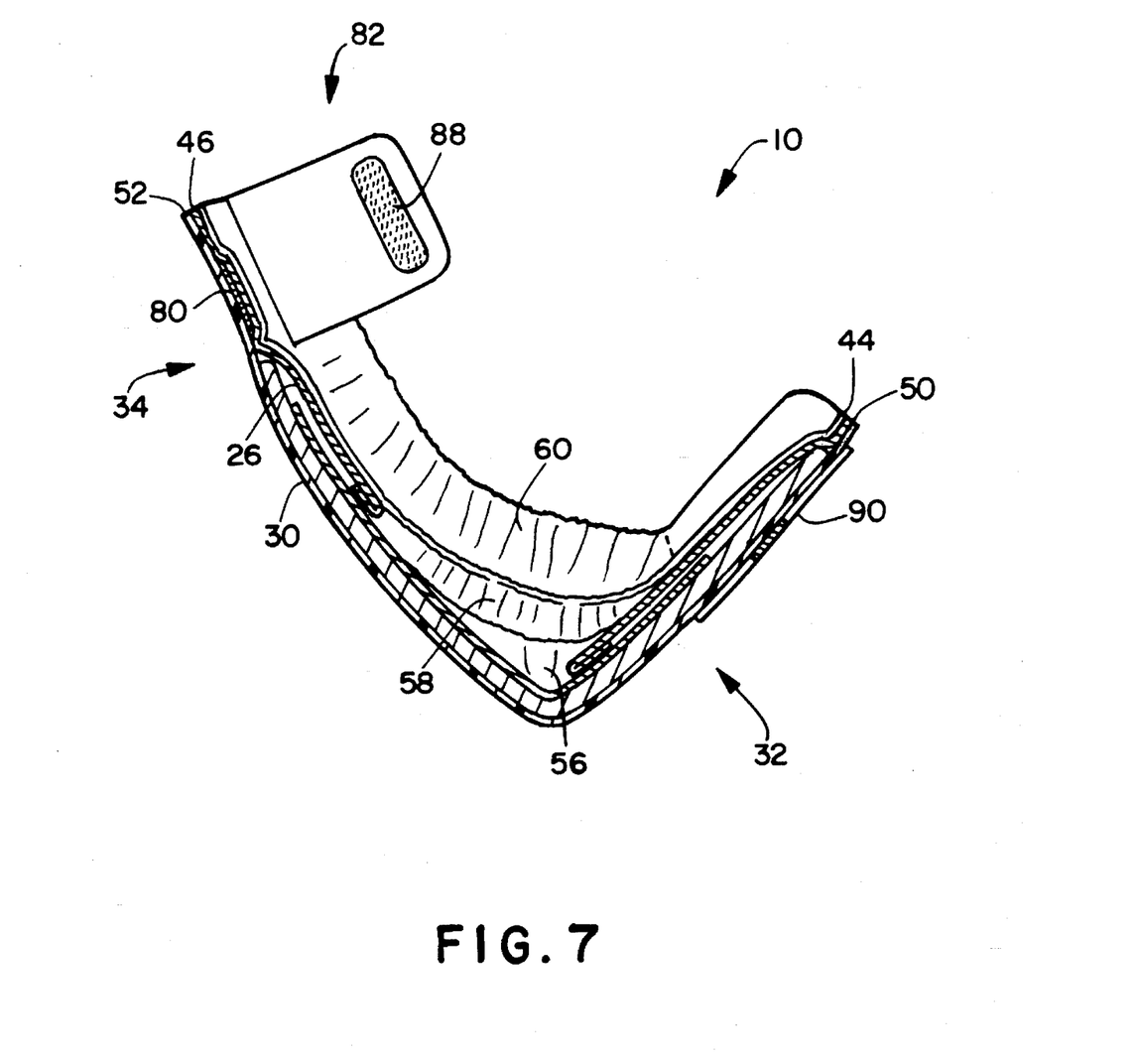
FIG. 7 is a cross-sectional view of FIG. 5 taken along line 7—7 and viewed in the direction of the arrows.
Figure 8:
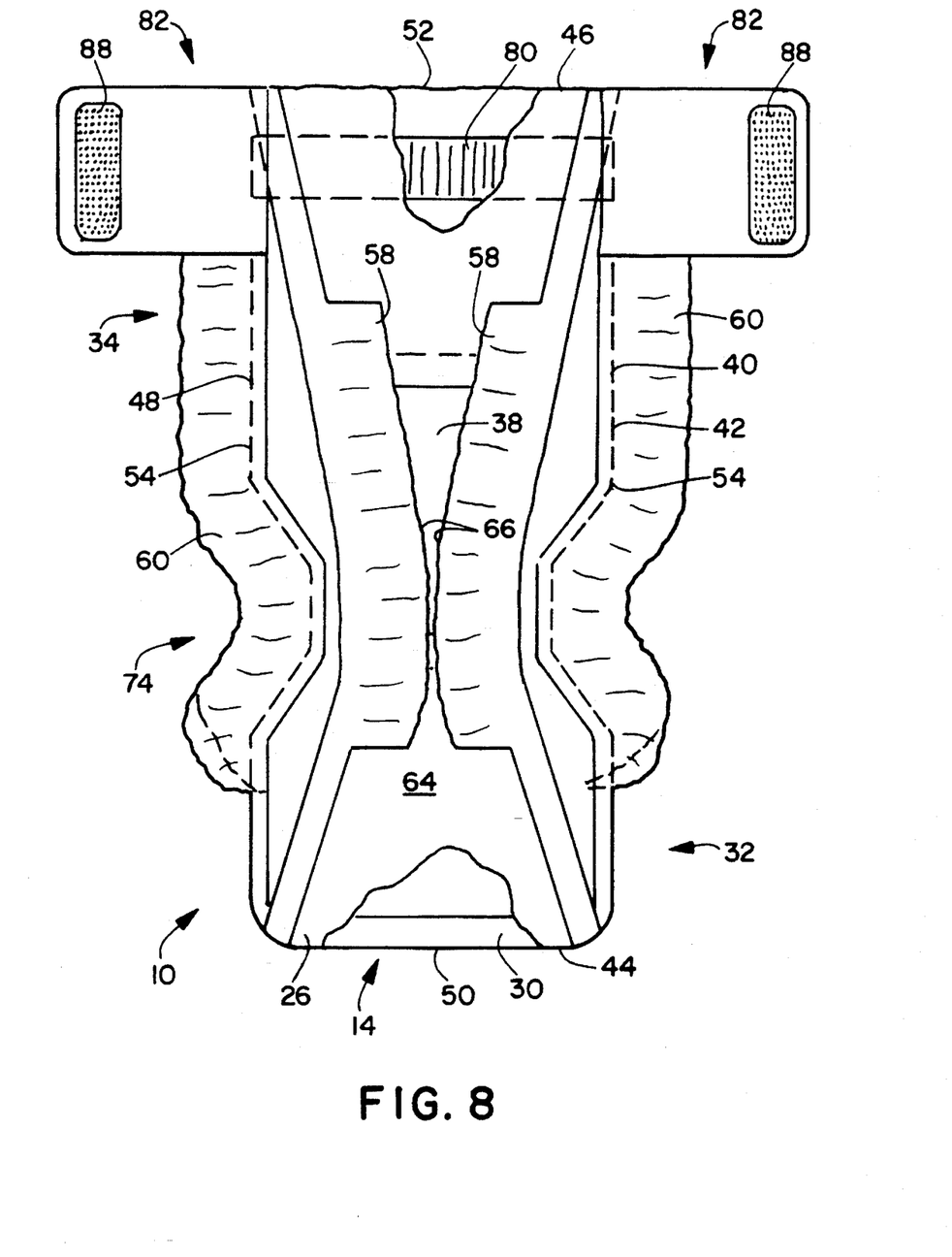
FIG. 8 is a top plan view of a diaper of the present invention.

Topsheet 26 has periphery 40 defined by front longitudinal end 44, back longitudinal end 46, and lateral sides 48. Similarly, backsheet 30 has periphery 42 defined by front longitudinal end 50, back longitudinal end 52, and lateral sides 54. Periphery 42 has a peripheral length or measurement greater than that of periphery 40. Periphery 42 can be made to have a peripheral measurement greater than periphery 40 by making topsheet 26 more narrow than backsheet 30, or more shorter than backsheet 30, or both. When topsheet 26 is joined to backsheet 30 along their respective peripheries 40, 42, waste containment pocket 56 is formed therebetween (FIG. 7). Topsheet 26 and backsheet 30 can be joined or attached in any suitable manner, such as by a line or lines of adhesive bonding, thermal bonding, or ultrasonic bonding, and can be joined at their peripheral edges or slightly inboard thereof, for example, at a distance from about one-eighth inch to about three-eighths inch or more from the peripheral edges.

Absorbent structure 14 is positioned between topsheet 26 and backsheet 30, and is joined or attached to backsheet 30 by any suitable means, such as by lines or a surface spray of adhesive. Waste containment pocket 56 is then defined between absorbent structure 14 and topsheet 26. Waste containment pocket 56 is designed to receive and contain a volume of fecal matter of at least about 150 cubic centimeters.

A dual pair of flaps are also disposed on diaper 10, and are identified as containment flaps 58 and side flaps 60. Within the context of the present disclosure, the terms "disposed", "disposed on", "disposed with", and any variations thereof, are intended to mean as a minimum that one element can be formed integrally from another element, or one element can be separate structure joined to or placed with or near another element. Side flaps 60 can be formed from extensions of lateral sides 54 of backsheet 30 and/or lateral sides 48 of topsheet 26, or can be separate structural elements attached to backsheet 30 and/or topsheet 26. Preferably, side flaps 60 are made of liquid-impermeable material that is vapor-permeable for increased air circulation in the crotch region, but may be made, if desired, from a liquid and vapor impermeable material or a liquid and vapor permeable material. Side flaps 60 can also have selected portions that are liquid permeable with the remaining portions being liquid impermeable.

Containment flaps 58 are located inboard of side flaps 60, i.e., closer to longitudinal centerline 62 (FIG. 6) than flaps 60. Centerline 62 is illustrated through absorbent structure 14, but is also intended to be the centerline for topsheet 26, backsheet 30, and diaper 10. Containment flaps 58 can be integral extensions of liquid-permeable topsheet 26, or can be separate liquid-permeable elements attached or joined to topsheet 26 inboard of side flaps 60. Flaps 58, 60 border the lateral sides of opening 38, with containment flaps 58 being closer to opening 38 than side flaps 60. Containment flaps 58 can also have selected portions that are liquid permeable with the remaining portions being liquid impermeable. Flaps 58 can also be liquid impermeable.

In one embodiment, containment flaps 58 are separate elements attached or adhered to upper surface 64 of topsheet 26, and side flaps 60 are separate elements attached or adhered between topsheet 26 and backsheet 30. Containment flaps 58 include at least one elastic member 66 in each distal edge portion 68, and preferably at least two or more elastic members 66 in each distal edge portion 68. Elastic members 66 are positioned and secured within respective distal edge portions 68 in a stretched or elastically contractible manner, such that upon relaxing elastic member 66, containment flaps 58 gather or shirr as illustrated in FIGS. 5, 7.

In a similar manner, side flaps 60 have elastic members 70 attached in a stretched or elastically contractible condition within respective distal edge portions 72 of side flaps 60. As illustrated in FIG. 6, and with reference to a single side flap 60 since both side flaps are identical, each side flap 60 comprises narrow end portions 76 with intermediate flap portion 78 extending therebetween in a preferably curvilinear fashion to accommodate and correspond to leg cut-outs 74.

One of the important aspects of the present invention is the various methods of disposing side flaps 60 with backsheet 30. In one method of positioning side flap 60 for attachment to backsheet 30, flap 60 is first pleated or elastically gathered, and thereafter attached or joined to backsheet 30 in the pleated or gathered state in a manner that does not pleat or gather backsheet 30. In this fashion, the overall, flattened-out length of intermediate flap portion 78 is longer than the flattened-out distance between points A and B on backsheet 30; points A and B being orthogonal projections of the remote ends of intermediate flap portion 78 on backsheet 30. Thus, upon pressing or flattening backsheet 30 against a flat surface, each intermediate flap portion 78 will have a shirred or ruffled appearance that is complemented by elastic members 70.

Another method of disposing flaps 60 with backsheet 30 is to maintain pleated or elasticized flaps 60 in a stretchedout state and then attach or join them to backsheet 30 to pleat or gather backsheet 30 upon relaxation thereof.

If desired, side flaps 60 can be designed without narrow end portions 76, and elastic members 70 can be attached the full length of diaper 10. Thereafter, selected portions of elastic members 70 can be de-elasticized by application of heat or other treatment dependent upon the material of which elastic members 70 are made.

Referring to FIGS. 5–8, disposable diaper 10 can also include waist elastics in the longitudinal end portions of front panel 32 and back panel 34. In one embodiment illustrated in FIG. 8, only back waist elastic 80 is joined to back panel 34, and can either be joined between backsheet 30 and topsheet 26 or joined only to backsheet 30 to allow greater elastic retraction. Waist elastic 80 is adhered or joined to back panel 34 in a stretched or elastically contractible condition, so that upon relaxation that portion of back panel 34 is gathered.

A pair of stretchable ears 82 are attached to opposite longitudinal sides of back panel 34, and are preferably in-line with back waist elastic 80. Since both of the stretchable ears 82 are identical, the following description will be made in terms of a single stretchable ear. Stretchable ear 82 comprises stretchable member 84 and stretchable band 86. Stretchable band 86 is connected to member 84 to aid in preventing stress failure to ear 82 and to apply additional elastic reinforcement to the center of ear 82. Both stretchable member 84 and stretchable band 86 are joined between backsheet 30 and topsheet 26, with band 86 preferably disposed on backsheet 30. Stretchable members 84 and/or stretchable bands 86 can be a stretch-bonded laminate.

Preferably, ears 82 are designed and manufactured as a single strip of elastic or stretchable material having the same stretch characteristics as the combination of stretchable member 86 and stretchable band 84.

To fit and maintain disposable diaper 10 on the wearer, a hook-and-loop fastening system is provided with tabs 88 of hook material joined to the side of stretchable member 84 opposite band 86, and panel 90 of loop material joined to backsheet 30. Although hook-and-loop fasteners are preferred, other fastening arrangements can be used, such as tapes, snap fasteners, and the like.

In one embodiment, backsheet 30 is made of a liquid-impermeable material, and preferably a polyethylene film having a thickness of about 1.0 mil, although thicknesses above 0.50 are functional. Backsheet 30 is generally flat, i.e., not pleated or microcreped, and has a peripheral measurement greater than the peripheral measurement of topsheet 26. In joining backsheet 30 and topsheet 26 to form waste containment pocket 56, periphery 42 of backsheet 30 needs to be drawn inwardly to be joined to periphery 40 of topsheet 26. One method of forming backsheet 30 in this manner is by vacuum forming backsheet 30 into a mold of predetermined shape and dimensions that result in waste containment pocket 56 having a preferred shape.

In another embodiment, additional useable volume in waste containment pocket 56 is included by providing (1) a means for the feces to pass through or around the absorbent core, for example, a trapezoidal-shaped hole in the absorbent having a rear width of about 1.5 inches, a front width of about 1 inch, and sloping side lengths of about 4 inches; and (2) an outer barrier sheet, such as backsheet 30, having dimensions longer than the topsheet and absorbent core and having a space formed between backsheet 30 and the absorbent core so as to contain the fecal material between the absorbent and the backsheet.

Other means of providing additional useable volume in pocket 56 by using backsheet 30 include (a) using an embossed film which can expand easily, (b) making the backsheet from a low modulus, easily elongatable film, such as "KRATON" styrene-butadiene elastomer or ethyl vinyl acetate (EVA), (c) creping an ordinary film in the same method that tissue is creped to form creped wadding, (d) forming pleats in the machine direction or cross direction in the backsheet or only portions of the backsheet which can easily expand, and (e) thermal forming a bulge in the crotch area of the backsheet. Alternatively, topsheet 26 can be made of a stretchable material and cut shorter and/or narrower than backsheet 30, and then peripherally joined to backsheet 30 to provide additional useable volume.

The total volume to handle fecal matter should be at least about 150 cubic centimeters. The amount of expandability required in backsheet 30 depends on the desired degree of reduction in fecal smearing, the volume of fecal material the design is intended to handle, and the volume of the hole provided in absorbent 14 when the wearer is in the sitting position. For example, since normally 60 cubic centimeters or less of fecal material would be expelled in one defecation and if the volume of the hole in the absorbent would be about 20 cubic centimeters, then the expandability of the backsheet should handle about 40 cubic centimeters.

In order to provide this volume, experience has shown that a desirable range of expandability of backsheet 30 is from about 20% to about 100%. The exact amount is dependent on a wide range of variables including the baby's position during defecation, tightness of the baby's clothing, viscosity of the fecal material, pressure exerted by the topsheet against the body, resistance of the material to the expansion force of the bowel movement, rate of expulsion of the fecal material from the body and rigidity of the absorbent material. Materials that readily expand about 20% or more under a force of about 25 grams per inch of width or less function adequately and can expand sufficiently to accommodate normal volume bowel movements.

Another method for fecal management would be to have a normal, non-expandable backsheet in combination with an absorbent with a hole in the absorbent; the hole having about 20 cubic centimeters to about 60 cubic centimeters volume. Also required would be a topsheet with a hole or holes sufficient to allow fecal material to pass through, and which substantially fully contacts the body along a line through the crotch from the front end of the diaper to the back. The hole can be covered or masked with an opaque material disposed between the topsheet and absorbent. Within the context of the present disclosure, the term "substantially fully contacts," and any variations thereof, is intended to mean as a minimum that topsheet 26 is sufficiently close to the body to prevent misalignment between the hole in topsheet 26 and the anus. A major portion of the upper surface, i.e., body-facing, surface area of topsheet 26 will be in contact with the skin of the wearer, except those areas of topsheet 26 that overlie the natural crevices or folds of a baby's body, such as the crevice between the baby's buttocks and the folds of skin at the juncture between the inner thighs and crotch. Naturally, if topsheet 26 has a plurality of small holes or a single larger opening therein, topsheet 26 will not contact the skin at those holes or openings. "Substantially fully contacts" can also be defined as that percent of topsheet 26 in contact with skin, for example, about 70% to about slightly less than 100% of topsheet 26 being in contact with the baby's skin.

Backsheet 30 may also be made of other materials that are suitably liquid-impermeable or treated to be so. Examples are meltblown or film material made of polypropylene or polyolefin copolymers such as ethylene vinyl acetate, ethylene methyl acrylate, ethylene ethyl acrylate, polyvinyl chloride, and the like. Other materials include a single spunbonded layer of the above types of materials, two layers of spunbonded and meltblown materials, or three layers of material of spunbonded-meltblown-spunbonded material, each of which is suitably treated or coated to be liquid-impermeable. These same materials may also be provided in laminate form. The spunbond materials provide an added feature of a cloth-like texture to backsheet 30.

Referring to FIG. 6, backsheet 30 may be made of a material that is not only liquid-impermeable, but also vapor-permeable. Alternatively, backsheet 30 can have a breathable panel 92 positioned adjacent or near longitudinal end 50. As illustrated in FIG. 6, breathable panel 92 and loop panel 90 may be coextensive, such that loop panel 90 forms an outer layer for breathable panel 92. However, it may be preferred that panel 92 and panel 90 be separate, i.e., not coextensive. The plurality of loops on loop panel 90 can function as heat-transfer elements that assist in reducing condensation on the diaper exterior.

Other designs include positioning panel 92 in backsheet 30 adjacent or near back longitudinal end 52, or adjacent or near both back longitudinal end 52 and front longitudinal end 50. Breathable panel 92 has a water vapor transmission rate (WVTR) value of at least about 2000 grams/square meter/24 hours. Preferably, panel 92 has a WVTR of at least about 4000 grams/square meter/24 hours, and more preferably has a WVTR of at least about 5000 grams/square meter/24 hours. Breathable panel 92 has a preferred effective breathable area of about 30 cm$^2$ and a preferred range of effective breathable area between about 20 to about 600 cm$^2$. The term "effective breathable area" refers to that area of breathable panel 92 that does not have any elements, materials or other structure, whether in particulate or fibrous or other form, obstructing or minimizing it that effectively negate its breathable characteristics.

Breathable panel 92 can comprise a microporous polymer film, such as Grade TMP-1 film manufactured by Mitzui Toatsu Chemical, Inc., Tokyo, Japan; a nonwoven fibrous material, such as a spunbonded or meltblown web composed of synthetic polymer fibers; or a calendared, composite, fibrous web which includes a barrier layer comprising fine fibers and a reinforcing layer comprising coarse fibers. The barrier layer and reinforcing layer are securely bonded together by fusing or adhering the reinforcing fibers into the barrier fibers, and the reinforcing layer is configured to conform to the outwardly facing surface of the composite web. If desired, loop panel 90 can serve as the reinforcing layer of breathable panel 92. For purposes herein, a fiber is "fine" if it has a diameter equal to or less than about 3 microns; and a fiber is "coarse" if it has a diameter equal to or greater than about 15 microns.

Breathable panel 92 has a transverse dimension, relative to longitudinal centerline 62, within the range of about 5 to about 25 centimeters, and a longitudinal dimension within the range of about 3 to about 15 centimeters. Panel 92 extends over about 10% to about 50% of the transverse dimension of absorbent structure 14.

Topsheet 26 can be a liquid-permeable, hydrophilic or hydrophobic material, such as a spunbonded web composed of synthetic polymer filaments; a spunlace web; a spunbond-meltblown web; a meltblown web; or a bonded-carded-web composed of synthetic polymer fibers. Suitable synthetic polymers include polyethylene, polypropylene, polyester, and nylon. In one embodiment, the polymer filaments have a denier within the range of about 1.5 to about 7 d., and preferably within the range of about 1.2 to about 6.0 d. The filaments are arranged to form a layer having a basis weight within the range of about 10 to about 35 gm/m$^2$ (gsm), and preferably a basis weight of about 20 gsm. Topsheet 26 has a bulk thickness within the range of about 0.0140 to about 0.0432 centimeters, and preferably within the range of about 0.0180 to about 0.305 centimeters. The bulk thickness is measured under a restraining pressure of about 0.014 psi.

Topsheet 26 also can be a "KRATON" styrene-butadiene elastomer meltblown/polypropylene spunbond stretch-bonded laminate which has been made wettable by addition of surfactants; a polyurethane spunbond material such as that manufactured by Kanebo Synthetic Fibers Company, Osaka, Japan, and made wettable by addition of surfactants; an elastomeric film made from elastomers such as rubber, latex rubber, polyurethane, "KRATON" styrene-butadiene elastomer, and the like, which has been perforated to allow fluid passage; a polyurethane foam which has been perforated to allow fluid passage; and a nonwoven which has been gathered through the use of elastic or other means, e.g., heat-shrinkable fibers, to produce an elastically stretchable material.

Containment flaps 58 and side flaps 60 can be made of the same material as topsheet 26, and can be integrally formed therefrom or can comprise separate structure joined to topsheet 26 in any suitable manner.

Each containment flap 58 preferably comprises a single layer having a basis weight of about 0.4 ounces per square yard (osy) that is folded upon itself to make a dual-layer flap having a basis weight of about 0.8 osy. For example, containment flaps 58 preferably comprise at least one layer of a nonwoven such as a spunbond, bonded-carded web, or spun-lace material comprised of polymers such as polypropylene, polyethylene, polyester, or nylon. The material is made wettable by the use of surfactants, such as "TRITON" or "AEROSOL OT". An example of such a containment flap is produced by folding a layer of 0.4 osy Triton-treated spunbond polypropylene over an elastomeric material to produce a two-layer flat material.

Elastic members 66 can be any suitable elastic material, such as natural rubber, synthetic rubber, or thermoplastic elastomeric polymers, and can be single or multiple threads or ribbons thereof. Optionally, these materials can be heat-shrinkable or heat-elasticizable. Preferably, elastic members 66 each comprise two strands of 470 Decitex "LYCRA" (Decitex being the weight in grams of a single thread which is 10,000 meters long), and at 90% of ultimate elongation provide a tension between about 25 grams to about 75 grams. The material permits containment flaps 58 to retract from about 30% to about 80% of their elongated length. More preferably, the material has about 50 grams force after one minute hold-time at 90% of ultimate elongation and the ability to retract to at least about 50% of the original length.

Side flaps 60 preferably comprise two layers of 0.8 osy spunbonded polypropylene, and can be liquid permeable, liquid impermeable, or liquid impermeable-vapor permeable. For example, side flaps 60 can comprise at least one layer of a nonwoven, such as a spunbonded, bonded-carded web, or spun-laced material comprised of polymers such as polypropylene, polyethylene, polyester, or nylon. The material is preferably non-wettable (hydrophobic) in nature. This 0.8 osy side flap comprises a layer of 0.8 osy spunbonded polypropylene which is disposed over an elastomeric material to produce a two-layer flap material.

Elastic members 70 can be made of the same material as elastic members 66. Preferably, elastic members 70 each comprise 3 strands of 620 Decitex "LYCRA", and at an elongation of 90% of ultimate elongation provide a tension between about 50 to about 150 grams. The material permits side flaps 60 to retract from about 30% to about 80% of their elongated length. More preferably, the material has about 50 grams force after one minute hold-time at 90% of ultimate elongation and the ability to retract to at least about 45% of the original length.

Stretchable ears 82 can be made of any suitable material having elastic or stretchable properties. Some examples of such materials are a stretch-bonded laminate comprising two gatherable layers of about 0.4 osy polypropylene spunbond having therebetween a layer of meltblown elastic material such as "KRATON" styrene-butadiene elastomer or polyurethane-based polymer. The layer of the elastomeric is stretched and then the two layers of polypropylene are joined thereto and upon relaxing the layers, the two polypropylene layers gather. Other stretch-bonded laminates can be produced from elastomeric film such as "KRATON" styrene-butadiene elastomer or urethane, elastomeric ribbons or threads such as "LYCRA", rubber, "PEBAX", urethane, or combinations thereof. The stretchable ears can also comprise alternative elastomeric materials, such as a stretchable urethane foam or polyurethane spunbond fabric similar to that manufactured by Kanebo. The stretchable ears can be made from a single elastomeric fabric or combinations of several elastomeric fabrics.

The position of hook tabs 88 on stretchable ears 82 and the position of loop panel 90 on backsheet 30 are important to the proper functioning of disposable diaper 10. Loop panel 90 should exclude about 1½ inches of the center of backsheet 30 to provide two loop sub-panels 91, 93. Loop sub-panels 91,93 should be placed about ¾ inch from the lateral sides 54 of backsheet 30. This is designed to ensure engagement between hook tab 88 and loop panel 90 in preferred areas. For example, if hook tabs 88 are positioned too near centerline 62 of backsheet 30, that tension created by stretchable ears 82 can cause (1) the elastic material to stretch beyond its elastic limits, (2) front panel 32 to droop or fold-over, and (3) red-markings on the skin; or if hook tabs 88 engage loop panel 90 too near lateral sides 54, that tension created by stretchable ears 82 can cause red marking on the skin. The loop panel width being larger than the width of the hook tab width allows the user some adjustment for baby waist dimension differences. Proper ear tension will improve attachment between the hooks and loops, and can prevent front panel droop caused by low tensions of about 300 grams or less and red marking of the skin or other irritation caused by high tensions above about 1200 grams. Tensions of at least about 100 grams are required to improve attachment between the hooks and loops. Proper ear tensions fall generally within the range of about 300 grams to about 1200 grams to prevent front panel droop.

Preferably, the width of ears 82 should be about 1.5 inches to about 2.5 inches, and the elastic force band should be preferably about 1.25 inches to about 2.25 inches above the front edge of the absorbent pad.

Ears 82 can be designed with higher tensions through the center and lower tensions outside these higher tension bands. Ears 82 also can be designed with uniform tension throughout the material.

Absorbent structure 14 can comprise surge portion 98 and retention portion 100. Surge portion 98 is in liquid communication with retention portion 100, and temporarily stores up to about 100% of a liquid insult, and subsequently releases liquid to retention portion 100. As illustrated, surge portion 98 is generally rectangular-shaped having a weight range of about 0.5 to about 15 grams of material and a surface area of about 10 square inches to about 50 square inches, and is positioned between the longitudinal ends of absorbent structure 14 and centered along centerline 62. Surge portion 98 overlies retention portion 100, which is of generally hour-glass shape. Other geometric forms and placements of surge portion 98 and retention portion 100 are contemplated by the present invention, such as surge portion 98 being disposed within retention portion 100 to form a single-layer structure. If desired, surge portion 98 can be joined to retention portion 100 by a bonding and/or fiber entanglement mechanism, such as ultrasonic, adhesive, or thermal bonding, or mechanical or hydraulic needling. Surge portion 98 can extend the full length of absorbent structure 14, or can be shorter in length and disposed in or near the front or back of absorbent structure 14.

Absorbent structure 14 can be manufactured in various shapes and with selected absorbent capacities compatible with the size of and the liquid loading imparted by the intended wearer.

A capillary force differential created at the interface between surge portion 98 and retention portion 100 can improve the characteristics of absorbent structure 14. If surge portion 98 has and maintains relatively lower capillary attraction compared to the capillary attraction of retention portion 100, liquid surges will tend to be desorbed more readily from surge portion 98 into retention portion 100.

Retention portion 100 can comprise various types and mixtures of fibrous material. For example, retention portion 100 may comprise cellulosic fluff, synthetic fibers, absorbent gelling materials in the form of particles, fibers, layers and the like, and various mixtures or blends thereof. Suitable absorbent gelling materials can be inorganic materials such as silica gels, or organic compounds such as cross-linked polymers. Some examples of absorbent gelling material polymers include polyacrylamides, polyvinyl alcohol, polyacrylates, and the like. Other acceptable polymers include acrylonitrile grafted starch, acrylic acid grafted starch, modified carboxy methyl cellulose, and the like.

Retention portion 100 can also comprise a mixture of about 1% to about 30% by weight of an inherently wettable polymer, such as "HYDROFIL", polyester, "PEBAX", or wettable polyethylene or polypropylene; about 5% to about 90% by weight absorbent gelling material; and about 20% to about 80% by weight cellulosic fluff. More preferably, retention portion 100 can be about 2% to about 15% by weight of an inherently wettable polymer, about 15% to about 50% by weight absorbent gelling material, and about 45% to about 70% by weight cellulosic fluff. Retention portion 100 can have a basis weight in the range of about 200 to about 3000 gsm. A preferred range is between about 500 to about 1000 gsm. A more preferred basis weight is about 900 gsm. Retention portion 100 can have a density in the range of about 0.08 to about 0.40 g/cc. A preferred range is between about 0.15 to about 0.30 g/cc. A preferred density is about 0.22 g/cc. With respect to the density measurement of retention portion 100, it is calculated from its basis weight and thickness, and is measured on newly unpacked, unfolded, and desiccated diapers.

Surge portion 98 can comprise the same types of materials as retention portion 100. Preferably, surge portion 98 comprises "HYDROFIL" material having a basis weight between about 100 to about 600 gsm, a density between about 0.05 to about 0.15 g/cc, and a surface area between about 10 to about 50 square inches, i.e., about 64.5 to about 322 centimeters square. Preferably, surge portion 98 has a basis weight of about 400 gsm, a density of about 0.1 g/cc and a surface area of about 25 square inches.

The entire absorbent structure 14 can be wrapped in a hydrophilic web made of the same material as topsheet 26, a wood fiber tissue, or a powder-bonded polyester carded web having a basis weight between about 15 to about 30 gsm.

While this invention has been described as having preferred embodiments, it will be understood that it is capable of further modifications. This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. A disposable absorbent article, comprising:
   a liquid permeable topsheet including opposite longitudinal ends and opposite lateral sides, said ends and said sides forming a topsheet periphery having a topsheet peripheral measurement, and
   a liquid impermeable backsheet including opposite longitudinal ends and opposite lateral sides, said ends and said sides forming a backsheet periphery having a backsheet peripheral measurement greater than said topsheet peripheral measurement, said liquid impermeable backsheet further including a breathable panel positioned adjacent or near a longitudinal end thereof,
   said topsheet periphery being joined to said greater backsheet periphery to form a waste-containment pocket therebetween,
   said liquid permeable topsheet substantially fully contacting the body of the wearer when in use, the percentage of said liquid permeable topsheet in contact with the body being greater than about 70 percent,
   said liquid permeable topsheet further defining a hole sufficient to allow solid fecal matter to pass therethrough.

2. The article of claim 1 further comprising an absorbent structure located between said liquid permeable topsheet and said liquid impermeable backsheet, said absorbent structure having an overall width of from about 4 to about 7 inches and comprising a crotch portion having a crotch width of from about 2 inches to about 3 inches.

3. The absorbent article according to claim 1 wherein said backsheet is expandable.

4. The absorbent article according to claim 1 wherein said topsheet is stretchable.

5. The article of claim 1 further comprising an absorbent structure located between said liquid permeable topsheet and said liquid impermeable backsheet, said absorbent structure defining a hole having a volume.

6. The article of claim 5 wherein said hole defined by said absorbent structure has a volume of from about 20 cubic centimeters to about 60 cubic centimeters.

7. A disposable absorbent article, comprising:
   a liquid permeable topsheet having opposite lateral sides,
   a liquid impermeable backsheet including a breathable panel positioned adjacent a longitudinal end thereof,
   and an absorbent structure being disposed between said liquid permeable topsheet and said liquid impermeable backsheet, said absorbent structure having an overall width of from about 4 to about 7 inches and comprising a crotch portion having a crotch width of from about 2 inches to about 3 inches, whereby said crotch portion fits conformably to the wearer's crotch.

8. The article of claim 7 further comprising a pair of stretchable ears at one longitudinal end of said article, said stretchable ears having one of a plurality of loop members and a plurality of hook members thereon, an opposite longitudinal end of said article having the other of said plurality of loop members and said plurality of hook members thereon.

9. The article of claim 7 wherein said absorbent structure has an overall width less than about 5 inches.

10. The article of claim 7 further comprising a pair of containment flaps positioned at respective ones of said lateral sides of said topsheet, and
   a pair of side flaps positioned at respective ones of said lateral sides of said topsheet.

11. The article of claim 10 wherein selected portions of said containment flaps are liquid permeable and remaining portions of said containment flaps are liquid impermeable.

12. The article of claim 10 wherein selected portions of said side flaps are liquid permeable and remaining portions of said side flaps are liquid impermeable.

13. The absorbent article according to claim 7 wherein said backsheet is expandable.

14. The absorbent article according to claim 7 wherein said topsheet is stretchable.

15. The absorbent article according to claim 7 wherein said liquid permeable topsheet defines a hole sufficient to allow solid fecal material to pass therethrough and said absorbent structure defines a hole.

16. The absorbent article according to claim 15 wherein said hole defined by said absorbent structure has a volume of from about 20 to about 60 cubic centimeters.

* * * * *